(12) United States Patent
Levy et al.

(10) Patent No.: US 11,027,218 B2
(45) Date of Patent: Jun. 8, 2021

(54) PURIFICATION AND SEPARATION TECHNIQUES FOR CANNABINOIDS

(71) Applicant: Canopy Growth Corporation, Ontario (CA)

(72) Inventors: Kurt Aron Levy, Dillon, CO (US); Karl Enmark, Lakewood, CO (US)

(73) Assignee: Canopy Growth Corporation, Ontario (CA)

( * ) Notice: Subject to any disclaimer, the term of this patent is extended or adjusted under 35 U.S.C. 154(b) by 0 days.

(21) Appl. No.: 16/308,421

(22) PCT Filed: Jun. 9, 2017

(86) PCT No.: PCT/US2017/036792
§ 371 (c)(1),
(2) Date: Dec. 7, 2018

(87) PCT Pub. No.: WO2017/214529
PCT Pub. Date: Dec. 14, 2017

(65) Prior Publication Data
US 2019/0192993 A1   Jun. 27, 2019

Related U.S. Application Data

(60) Provisional application No. 62/508,129, filed on May 18, 2017, provisional application No. 62/348,445, filed on Jun. 10, 2016.

(51) Int. Cl.
| | |
|---|---|
| *B01D 11/02* | (2006.01) |
| *C07D 311/80* | (2006.01) |
| *B01D 15/40* | (2006.01) |
| *C07C 39/19* | (2006.01) |
| *C07C 39/23* | (2006.01) |
| *C30B 7/00* | (2006.01) |
| *C30B 29/54* | (2006.01) |
| *B01D 9/00* | (2006.01) |

(52) U.S. Cl.
CPC .......... *B01D 11/0292* (2013.01); *B01D 11/02* (2013.01); *B01D 11/0207* (2013.01); *B01D 11/0265* (2013.01); *B01D 11/0288* (2013.01); *B01D 15/40* (2013.01); *C07C 39/19* (2013.01); *C07C 39/23* (2013.01); *C07D 311/80* (2013.01); *C30B 7/00* (2013.01); *C30B 29/54* (2013.01); *B01D 9/00* (2013.01)

(58) Field of Classification Search
CPC ...................... B01D 11/0261; B01D 11/0292
See application file for complete search history.

(56) References Cited

U.S. PATENT DOCUMENTS

| | | |
|---|---|---|
| 7,700,368 B2 | 4/2010 | Flockhart et al. |
| 8,445,034 B1 | 5/2013 | Coles, Jr. |
| 2009/0012277 A1* | 1/2009 | Ma ........................... C07J 71/00 536/5 |

FOREIGN PATENT DOCUMENTS

| | | | | |
|---|---|---|---|---|
| CN | 104277917 A | * | 1/2015 | |
| WO | WO-2016187679 A1 | * | 12/2016 | .............. A61P 25/06 |

* cited by examiner

*Primary Examiner* — John S Kenyon
(74) *Attorney, Agent, or Firm* — Sheridan Ross P.C.

(57) ABSTRACT

This disclosure relates to techniques and methods to isolate and purify cannabinoids, such as CBDV, CBD, CBC, THCV, THC, CBN, CBG, CBDA, THCA, or CBGA. Evaporation and sonicating techniques are used to isolate and purify cannabinoids, such as CBDV, CBD, CBC, THCV, THC, CBN, CBG, CBDA, THCA, or CBGA. The resulting compounds find further use within the devices and compositions described herein as well as for preparative and analytical methods.

8 Claims, 4 Drawing Sheets

PURIFICATION AND SEPARATION TECHNIQUES FOR CANNABINOIDS

CROSS REFERENCE TO RELATED APPLICATIONS

This application is a National Stage application under 35 U.S.C. 371 of International Application No. PCT/US2017/036792 having an international filed date of Jun. 9, 2017 which claims priority on the basis of U.S. Provisional Patent Application Ser. No. 62/348,445, filed on Jun. 10, 2016 and U.S. Provisional Patent Application Ser. No. 62/508,129, filed on May 18, 2017, each of which is hereby incorporated by reference.

TECHNICAL FIELD

This disclosure relates to the *cannabis* industry. In particular, this relates to purification and separation techniques.

BACKGROUND

The word "*cannabis*" refers to a genus of flowering plants. Plants of genus *cannabis* include several species, including *Cannabis sativa, Cannabis indica*, and *Cannabis ruderalis*. There is a long history of cultivating plants of genus *cannabis* for hemp fibers, seeds and seed oils, medicinal purposes, and recreational activities.

According to some accounts, *cannabis* is composed of at least 483 known chemical compounds, which include cannabinoids, terpenoids, flavonoids, nitrogenous compounds, amino acids, proteins, glycoproteins, enzymes, sugars and related compounds, hydrocarbons, alcohols, aldehydes, ketones, acids, fatty acids, esters, lactones, steroids, terpenes, non-cannabinoid phenols, vitamins, and pigments.

Cannabinoids are of particular interest for research and commercialization. Most extractions of *cannabis* plant matter aim to extract cannabinoids, particularly tetrahydrocannabinol (THC). THC is useful for relieving pain, treating glaucoma, and relieving nausea. THC is also gaining immense popularity as a recreational drug substance. Usually, cannabinoids are extracted from the *cannabis* plant as part of a crude mixture, combined with other chemical compounds found in the *cannabis* plant.

Many extraction processes have been developed for isolating and purifying these cannabinoids. But there has been difficulty in isolating individual cannabinoids at high levels of purity, both for active ingredients for use in medicine and product manufacturing and/or as standards for use in research and development. Gas chromatography has provided adequate samples of some cannabinoids, like THC, CBD, and CBN on a smaller scale. For larger preparative scales, methods of extraction include lipid extraction and butane hash oil (BHO) extraction.

In these existing methods, there exists variability and inconsistency with regards to which molecules are extracted from the plant. Accordingly, extractions vary considerably in chemical composition depending on the variety of plant used in the extraction and the extraction parameters used to purify the cannabinoid compounds.

There exists a need for separation techniques that yields a high purity of cannabinoids. There exists a need for separation and extraction techniques which provide reliable and consistent purified cannabinoid compositions. In particular, there exists a need for isolating purified cannabinoids on a scalable level.

DETAILED DESCRIPTION

Figure 1:
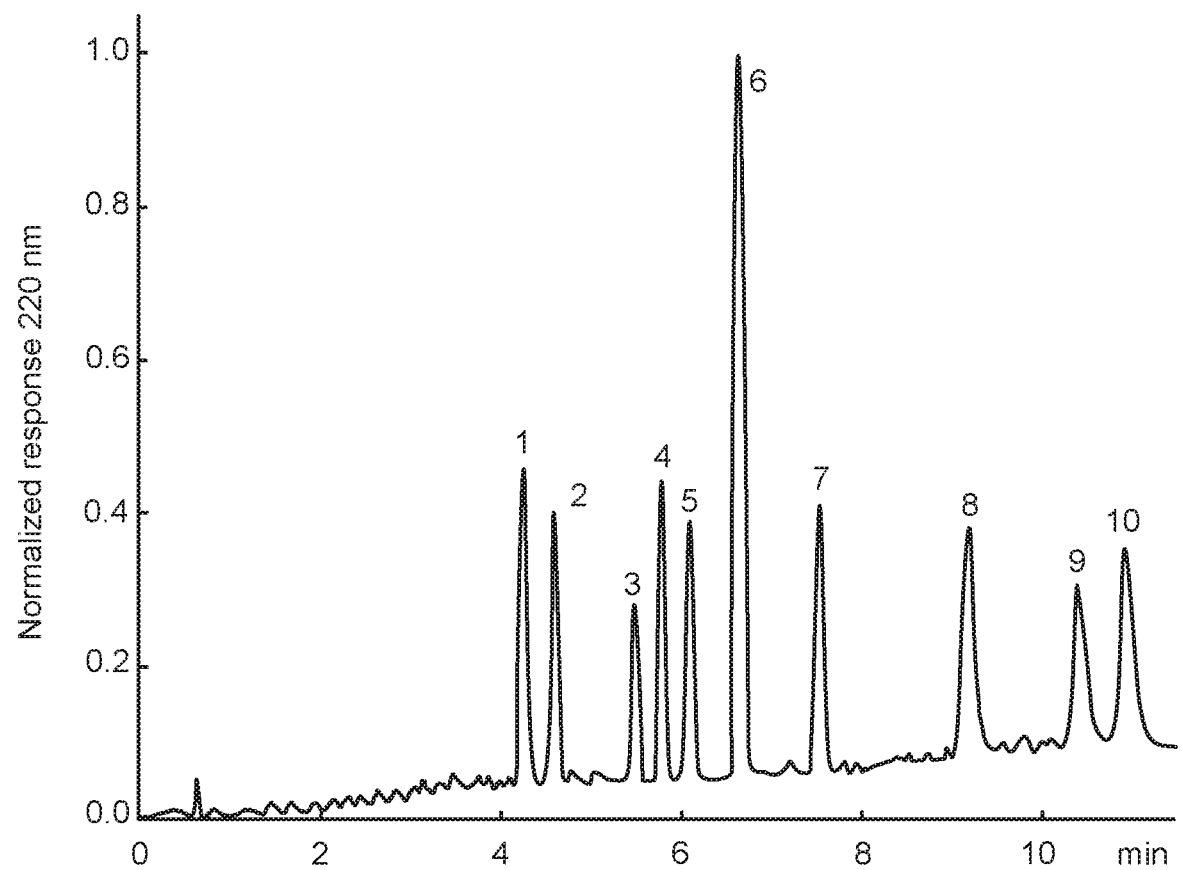
FIG. 1 illustrates a non-limiting example of the resolution of separating 10 cannabinoids using the methods disclosed herein.

Disclosed herein are new methods for purifying and separating one or more compounds from a plant of genus *cannabis*. In one embodiment, this disclosure provides a method of purifying a cannabinoid from a plant of genus *cannabis*. In one embodiment, this disclosure provides a method of purifying a terpene from a plant of genus *cannabis*. In one embodiment, this disclosure provides a method of purifying and separating a collection of cannabinoids from a plant of genus *cannabis*. In one embodiment, this disclosure provides a method of purifying and separating a collection of terpenes from a plant of genus *cannabis*. In one embodiment, this disclosure provides a method of purifying and separating a collection of cannabinoids and terpenes from a plant of genus *cannabis*.

In one embodiment, a cannabinoid is isolated from a plant of genus *cannabis* by sonication, extraction, and/or evaporation techniques. In some embodiments, extraction of a high purity cannabinoid is accomplished by applying a range of extraction temperatures. The purifying and separating techniques disclosed herein are scalable. In some embodiments, extraction of a high purity cannabinoid is accomplished on an analytical scale. In some embodiments, extraction of a high purity cannabinoid is accomplished on a preparative scale.

Additionally, Cellulose-2 is available in 3, 5, 10, and 20 µm particle size allowing for scalability of the disclosed methods at various levels of preparative scale. A chromatographer can use a pre-packed Axia preparative column, up to 50 mm diameter, or manually pack a column for further scale-up and large scale manufacturing production.

In one embodiment, the purifying and separating techniques comprise column chromatography. In one embodiment, the column length and particle size are held constant while the column diameter is increased.

In one embodiment, the particle size is between 1-20 µm.
In one embodiment, the particle size is between 3-25 µm.
In one embodiment, the particle size is between 5-15 µm.

Disclosed herein is a new product made from the aforementioned methods. In one embodiment, the product is suitable for formulating compositions. In one embodiment, the product is suitable as an analytical standard.

Disclosed herein is a new method of purifying secondary compounds, e.g., a cannabinoid, terpene, etc., from plant material, comprising:
  adding the plant material to alcohol;
  sonicating the alcohol and plant material;
  dissolving secondary compounds in the alcohol to create a solution of secondary compounds;
  physically separating the plant material from the solution comprising secondary compounds; and
  evaporating the alcohol from the solution.

As used herein, the term "purifying" means separating, extracting, and/or isolating a compound or compounds from other compounds, materials, matter, mass and/or substances. For example, within the context of this disclosure, the term "purifying" includes extracting or separating from other compounds, compositions, matter, or mass. For example, individual cannabinoid compounds "purified" vis-a-vis those occurring in the *cannabis* plant are separated from some or all other parts of the plant. In one embodiment, purifying provides a compound or compounds having purity significantly different than from crude extracts, a biological drug substance (BDS), plant matter, or formulations and compositions made from the same.

In one embodiment, the term purifying refers to separating a cannabinoid from the plant matter from which it was derived. In one embodiment, the purifying refers to separating a cannabinoid from other cannabinoids present in the plant matter from which it was derived. In one embodiment, the term purifying refers to separating a cannabinoid from terpenes present in the plant matter from which it was derived. In one embodiment, the term purifying refers to separating a cannabinoid from secondary compounds present in the plant matter from which it was derived. In one embodiment, the term purifying refers to separating a cannabinoid from all material that was present in the plant matter from which it was derived.

In one embodiment, the term purifying refers to separating a terpene from the plant matter from which it was derived. In one embodiment, the purifying refers to separating a terpene from other terpenes present in the plant matter from which it was derived. In one embodiment, the term purifying refers to separating a terpene from cannabinoids present in the plant matter from which it was derived. In one embodiment, the term purifying refers to separating a terpene from secondary compounds present in the plant matter from which it was derived. In one embodiment, the term purifying refers to separating a terpene from all material that was present in the plant matter from which it was derived.

Within the context of this disclosure, purified compounds may be purposely formulated with other compounds at various levels of purity. For example, depending on the desired outcome, a particular cannabinoid or terpene may be formulated with other molecules when it is 60-65% pure, 65-70% pure, 70-75% pure, 75-80% pure, 80-85% pure, 85-90% pure, 90-95% pure, 95-99% pure, 99-99.9% pure, 99.9+%, or greater than 99% pure. Provided that the ingredients used for purposeful formulation are purified prior to the said purposeful formulation, the act of subsequently formulating them does render them not "purified" within the context of an ingredient list.

In one embodiment, the compounds disclosed herein are purified by extracting the soluble compounds from plant material with ethanol.

In one embodiment, the compounds disclosed herein are purified through chromatography techniques, such as supercritical fluid chromatography.

In one embodiment, the purity of a purified cannabinoid is determined by chromatography, such as HPLC, GC-MS, or other known analytical methods.

In one embodiment, a cannabinoid and/or a terpene is purified from natural plant of genus *cannabis* by using a Novasep SuperSep 1000 preparative Supercritical Fluid Chromatography System, configured to collect fractions, each containing one or more of a cannabinoid or terpene.

In one embodiment, a cannabinoid and/or a terpene is purified from a natural plant of genus *cannabis* via chromatography on a polysaccharide-based stationary phase, e.g., cellulose column, e.g., 5 µm 250×4.6 mm cellulose column of Cellulose tris(3-chloro-4-methylphenylcarbamate).

In one embodiment, a cannabinoid and/or terpene is purified using a Jasco 50 preparative Supercritical Fluid Chromatography System. In one embodiment, the system is configured with open bed collection. In one embodiment, the system is configured to collect greater than 10 fractions. In one embodiment, the system is configured to collect greater than 20 fractions. In one embodiment, the system is configured to collect greater than 50 fractions. In one embodiment, the system is configured to collect greater than 100 fractions.

In one embodiment, a cannabinoid is purified by chromatography using a $CO_2$/ethanol gradient program.

In one embodiment, one or more cannabinoids are separated by chromatography and eluted from the column in the following order CBD; CBC; THCV; THC; CBN; CBG; CBDA; and THCA.

In one embodiment, one or more cannabinoids are separated by chromatography and eluted from the column in the following order CBDV; CBD; CBC; THCV; THC; CBN; CBG; CBDA; THCA; and CBGA.

In one embodiment, CBD is purified from hemp extract by using a 250×10 mm cellulose column with ethanol as an organic modifier under supercritical fluid chromatography conditions. In one embodiment, acidic cannabinoids, e.g., CBDA, THCA, CBDA, etc., are eluted at the end of the separation run, i.e., in the later fractions.

In one embodiment, THC is purified from a plant of genus *cannabis* on an analytical scale, e.g., 250×4.6 mm cellulose column. In one embodiment, THC is purified from a plant of genus *cannabis* on a preparative scale, e.g., 250×50 mm cellulose column.

As used herein, the term "plant material" means mass that is generated by a growing plant, including any compound or compounds (for example one or more secondary compounds) which may be later isolated. In one embodiment, the plant material is the stem of a plant. In one embodiment, the plant material is a trichome. In one embodiment, the plant material is a leaf. In one embodiment, the plant material is a flower. In one embodiment, the plant material is a whole plant. In one embodiment, the plant material is dried. In one embodiment, the dried plant material is ground.

As used herein, the term "alcohol" means an organic compound with a hydroxyl group attached to a carbon atom. In one embodiment, the alcohol is methanol. In one embodiment, the alcohol is ethanol. In one embodiment, the alcohol is propanol. In one embodiment, the alcohol is butanol.

As used herein, the term "sonicating" means using sound energy to agitate a particular portion of mass, for example by submerging a solid (e.g., plant material) into a liquid bath and then applying sound energy to the bath with the plant material in it.

As used herein, the term "dissolving" means incorporating a solid or gas substance into a liquid to create a homogenous liquid. In one embodiment, dissolving comprises heating. In one embodiment, dissolving comprises stirring. In one embodiment, dissolving comprises mixing. In one embodiment, dissolving comprises sonicating.

As used herein, the term "solution" means a homogeneous liquid having one or more molecular substances included therein. In one embodiment, the solution is a mixture of an alcohol and plant material. In one embodiment, the solution is a mixture of an alcohol and at least one cannabinoid. In one embodiment, the solution is a mixture of an alcohol and a at least one terpene.

As used herein, the term "evaporating" means transforming a substance from the liquid phase to the gas phase. In one embodiment, evaporating comprises heating. In one embodiment, evaporating comprises manipulating pressure.

In one embodiment, the methods disclosed herein comprise evaporating the alcohol from the solution at a pressure of less than 1 atmosphere.

In one embodiment, the methods disclosed herein comprise sonicating the alcohol and plant material at a temperature of between about −80 to 30 degrees Celsius.

In one embodiment, the methods disclosed herein comprise sonicating the alcohol and plant material at a temperature of between about −50 to 10 degrees Celsius.

In one embodiment, the methods disclosed herein comprise sonicating the alcohol and plant material at a temperature of between about −30 to −10 degrees Celsius.

In one embodiment, the methods disclosed herein comprise sonicating the alcohol and plant material at a temperature of between about 20 to 60 degrees Celsius.

In one embodiment, the methods disclosed herein comprise collecting a precipitated cannabinoid from within an alcoholic solution of secondary compounds. In one embodiment, the cannabinoid is selected from: CBDV, CBD, CBC, THCV, THC, CBN, CBG, CBDA, THCA, or CBGA.

As used herein, the term "CBDV" refers to Cannabidivarin, which has the following structural formula:

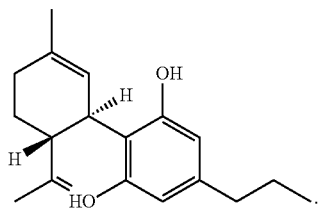

As used herein, the term CBD refers to Cannabidiol, which has the following structural formula:

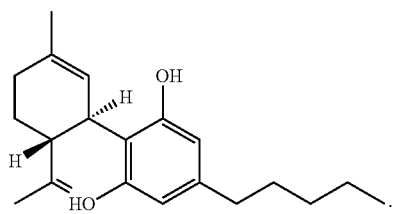

As used herein, the term "CBC" refers to Cannabichromene, which has the following structural formula:

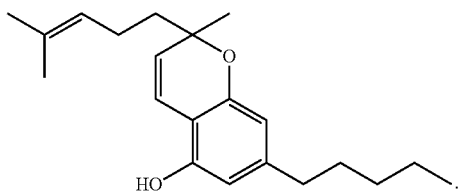 [SMILES: CCCCCc1cc(O)c2c(c1)OC(C)(CCC=C(C)C)C=C2]

As used herein, the term "THCV" refers to Tetrahydrocannabivarin, THV, THCv, THC-V, etc., which has the following structural formula:

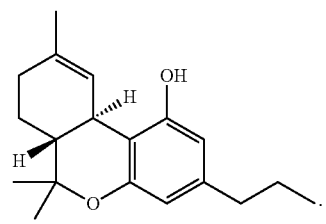 [SMILES: CCCc1cc(O)c2c(c1)OC(C)(C)[C@@H]1CCC(C)=C[C@@H]21]

As used herein, the term "THC" refers to Tetrahydrocannabinol, which has the following structural formula:

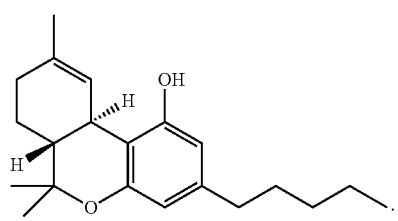 [SMILES: CCCCCc1cc(O)c2c(c1)OC(C)(C)[C@@H]1CCC(C)=C[C@@H]21]

As used herein, the term "CBN" refers to Cannabinol, which has the following structural formula:

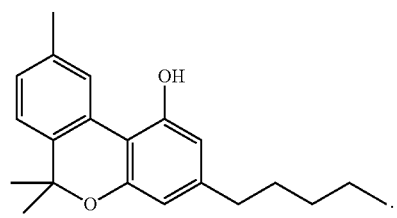 [SMILES: CCCCCc1cc(O)c2c(c1)OC(C)(C)c1ccc(C)cc1-2]

As used herein, the term "CBG" refers to Cannabigerol, which has the following structural formula:

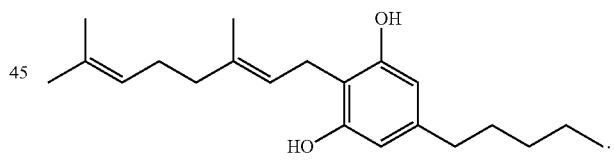

As used herein, the term "CBDA", "CBD-A", "CBDa", etc. refers to Cannabidiolic Acid, which has the following structural formula:

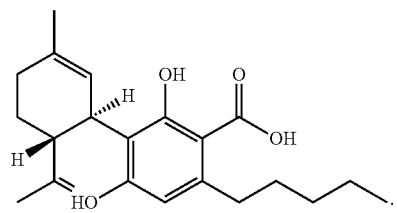

As used herein, the term "THCA", "THC-A", "THCa", etc., refers to Tetrahydrocannabinolic Acid, which has the following structural formula:

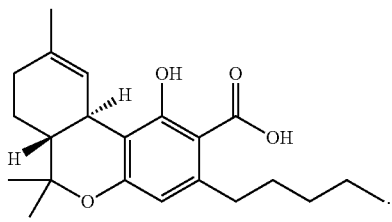 [SMILES: CCCCCc1cc2c(c(O)c1C(=O)O)[C@@H]1C=C(C)CC[C@H]1C(C)(C)O2]

As used herein, the term "CBGA", "CBG-A", "CBGa", etc., refers to Cannabigerolic Acid, which has the following structural formula:

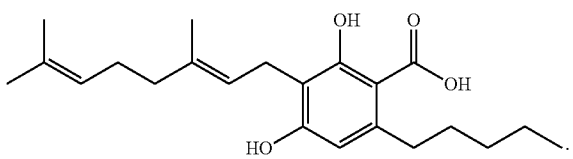 [SMILES: CCCCCc1cc(O)c(C/C=C(\C)CCC=C(C)C)c(O)c1C(=O)O]

As used herein, the term "precipitated cannabinoid" refers to a solid forming within and falling out of a liquid solution. In one embodiment, the precipitated cannabinoid forms by changing the temperature. In one embodiment, the precipitated cannabinoid forms by using a saturated solution. In one embodiment, the precipitated cannabinoid is selected from: CBDV, CBD, CBC, THCV, THC, CBN, CBG, CBDA, THCA, or CBGA.

In one embodiment, the methods disclosed herein comprise collecting the precipitated cannabinoid in an alcohol, creating a second solution, then recrystallizing the cannabinoid from the second solution.

As used herein, the term "recrystallizing" means to crystallize, or precipitate, a solid substance. In one embodiment, recrystallizing comprises dissolving a solid into a liquid and crystallizing the solid at least a second time. Typically, recrystallizing a substance results in higher purity.

In one embodiment, the methods disclosed herein comprise dissolving the precipitated cannabinoid in an alcohol, creating a second solution, then recrystallizing the cannabinoid from the second solution. In one embodiment, the alcohol is evaporated. In one embodiment, the alcohol is ethanol.

Disclosed herein is a new product produced by the method of purifying compounds from plant material, comprising:
    adding the plant material to alcohol;
    sonicating the alcohol and plant material;
    dissolving one or more compounds in the alcohol to create a solution of secondary compounds;
    physically separating the plant material from the solution comprising secondary compounds; and
    evaporating the alcohol from the solution.

In one embodiment, the products disclosed herein comprise a single crystal. In one embodiment, the products disclosed herein comprise a single crystal of a cannabinoid. In one embodiment, the cannabinoid is selected from: CBDV, CBD, CBC, THCV, THC, CBN, CBG, CBDA, THCA, or CBGA.

As used herein, the term "single crystal" means the crystal lattice of the entire sample is continuous and unbroken to the edges of the sample, with no grain boundaries.

In one embodiment, the single crystal of a cannabinoid is suitable for x-ray diffraction.

As used herein, the term "x-ray diffraction" refers to a rapid analytical technique primarily used for phase identification of a crystalline material and can provide information on unit cell dimensions.

Disclosed herein is a composition comprising a precipitated cannabinoid from within an alcoholic solution of secondary compounds.

Disclosed herein is a device comprising the product produced by the method of purifying secondary compounds from plant material, comprising:
    adding the plant material to alcohol;
    sonicating the alcohol and plant material;
    dissolving secondary compounds in the alcohol to create a solution of secondary compounds;
    physically separating the plant material from the solution comprising secondary compounds; and
    evaporating the alcohol from the solution, and attaching the resulting solid to a rigid support.

As used herein, a "rigid support" means a stiff structure supporting substance.

In one embodiment, the devices disclosed herein comprise a rigid transparent vessel;
    wherein said product is contained within said rigid transparent vessel; and
    wherein said rigid support means is contained within said rigid transparent vessel.

As used herein, a "rigid transparent vessel" means a firm storage device that is see through.

In one embodiment the devices comprise between 0.1 to 1.0 grams of the said product.

FIG. 1 illustrates one example of the resolution achieved by the disclosed methods using a Lux Cellulose-2 analytical column for separating 10 cannabinoids. Separating the cannabinoid standards with a baseline resolution was accomplished in less than 12 minutes on a 250×4.6 mm analytical column.

The disclosed method provides for optimization for specific cannabinoids. A smaller particle size, such as 3 µm, contributes to improved resolution and speed of analysis.

Chromatography also provides the ability for preparing the development work on a 250×4.6 analytical column. Then, keeping critical parameters, e.g., column packing, and conditions consistent, scale-up equations allow for scaling the separation method.

Figure 2:
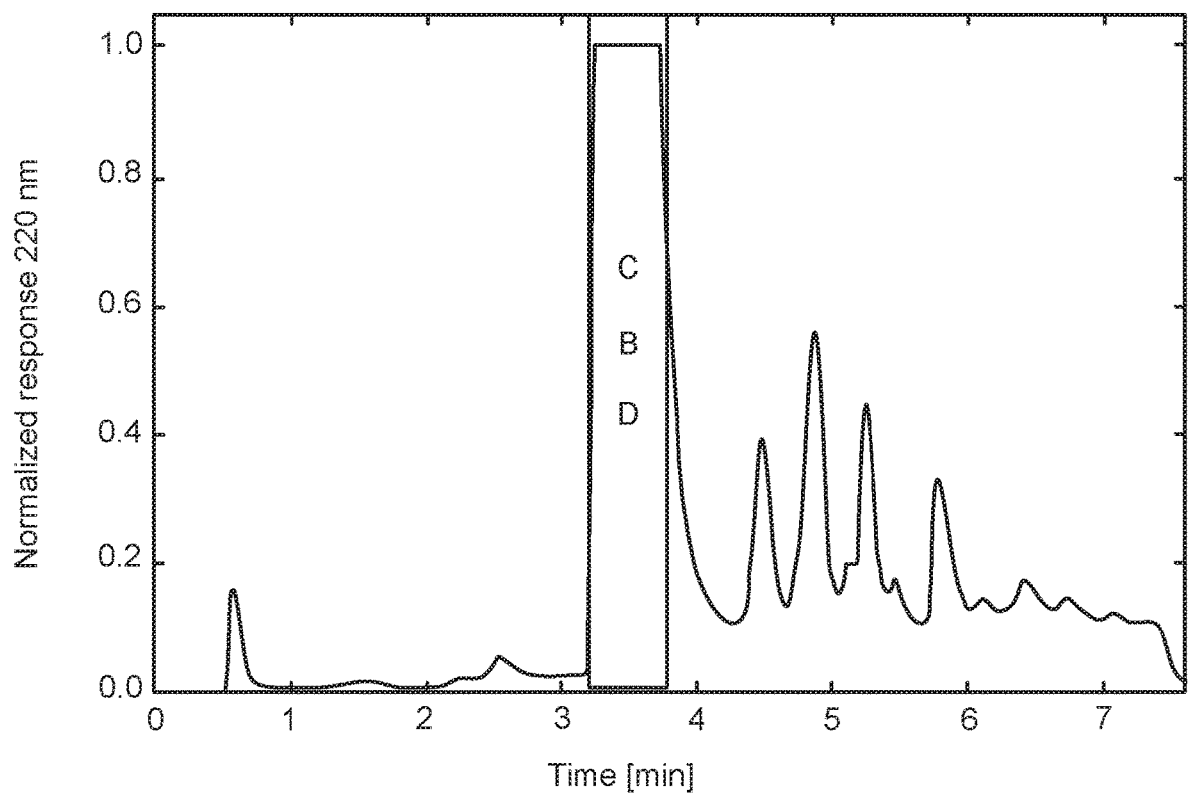
FIG. 2 illustrates a non-limiting example of the purification of CBD using the methods disclosed herein.

FIG. 2 illustrates a non-limiting example of purifying CBD from hemp extract using a Lux 5 um Cellulose-2 250×10 mm with ethanol as an organic modifier under SFC conditions.

The cycle time was 7 minutes and collected fractions were represented on a preparative chromatogram.

Figure 3:
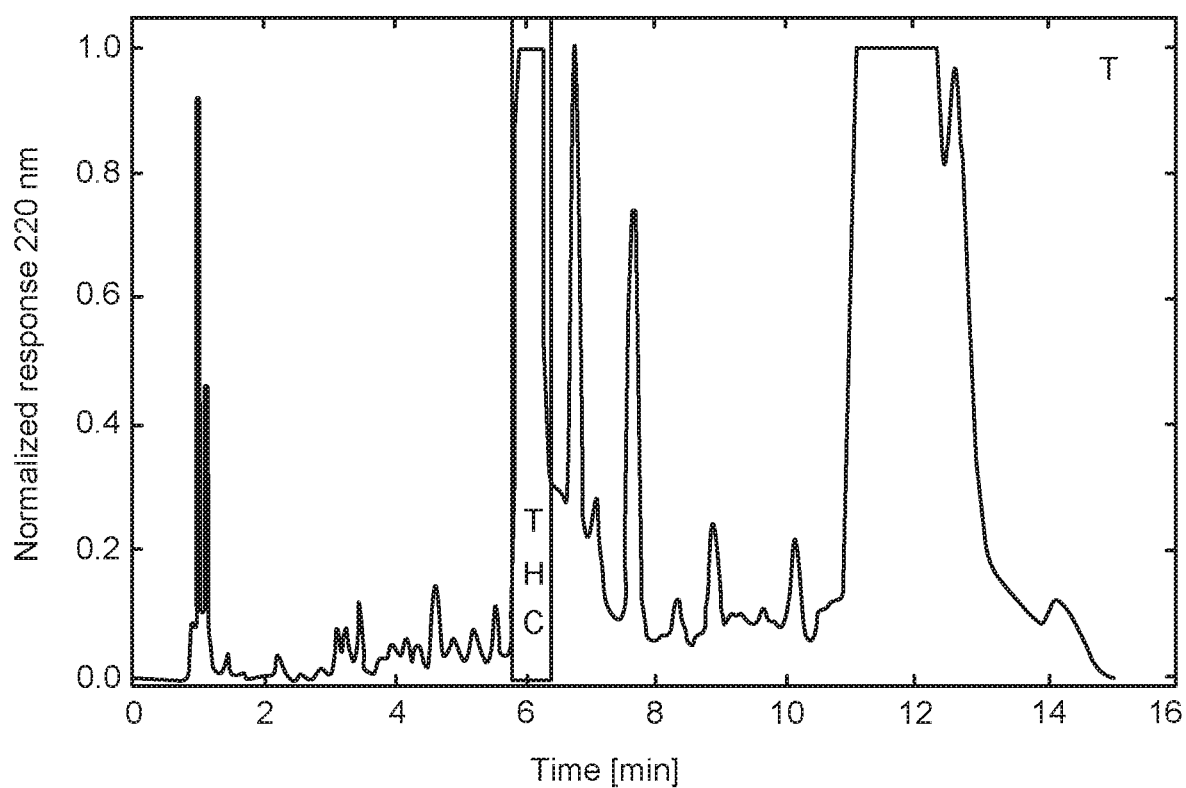
FIG. 3 illustrates a non-limiting example of the purification of THC using the methods disclosed herein.

FIG. 3 illustrates a non-limiting example of a separating THC from other molecules found in *cannabis*. The separation technique was developed on a 250×4.6 mm analytical column and scaled-up to a 250×50 mm Axia packed preparative column using a scale-up equation to preserve separation parameters.

Figure 4:
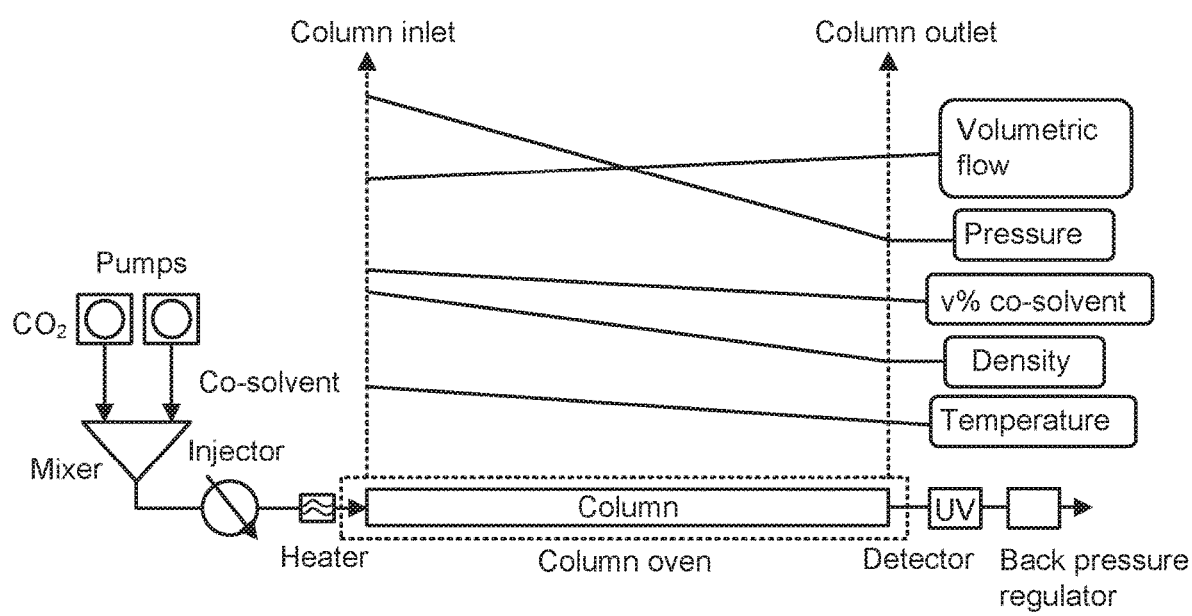
FIG. 4 illustrates a non-limiting example of axial gradients during SFC using the methods disclosed herein.

One method for achieving predictable scale-up from a bench-top instrument to a production instrument, including maintaining the column length and particle size while increasing the column diameter. This approach preserves the intrinsic conditions between 4.6 and 50 mm diameter columns. FIG. 4 illustrates a non-limiting example of typical axial gradients occurring during the methods disclosed herein.

EXAMPLES

The Cellulose-2 stationary phase was used for separating 10 cannabinoids (CBDV, CBD, CBC, THCV, THC, CBN, CBG, CBDA, THCA, and CBGA).

By using the Cellulose-2 stationary phase, the acid cannabinoids such as CBDA, THCA, and CBGA are eluted at the end of the separation under SFC conditions with ethanol as an organic modifier.

For purification on a column >50 mm ID, a bulk media was packed in a Dynamic Axial Compression (DAC) column. Lux Cellulose-2 was used with either 10 or 20 µm particle size. In some instances, the 10 µm particle size was a good compromise for batch processes using a single column.

Another example of the methods disclosed herein comprises separating 10 cannabinoids in less than 15 minutes by using SFC and a Lux Cellulose-2 column. This method was optimized for each cannabinoid by modifying the separation conditions.

The above examples are for illustrative purposes and are not meant to limiting or excluding subject matter.

Although the present invention herein has been described with reference to various exemplary embodiments, it is to be understood that these embodiments are merely illustrative of the principles and applications of the present invention. Those having skill in the art would recognize that various modifications to the exemplary embodiments may be made, without departing from the scope of the invention.

Moreover, it should be understood that various features and/or characteristics of differing embodiments herein may be combined with one another. It is therefore to be understood that numerous modifications may be made to the illustrative embodiments and that other arrangements may be devised without departing from the scope of the invention.

Furthermore, other embodiments of the invention will be apparent to those skilled in the art from consideration of the specification and practice of the invention disclosed herein. It is intended that the specification and examples be considered as exemplary only, with a scope and spirit being indicated by the claims.

Finally, it is noted that, as used in this specification and the appended claims, the singular forms "a," "an," and "the," include plural referents unless expressly and unequivocally limited to one referent, and vice versa.

As used herein, the term "include" or "comprising" and its grammatical variants are intended to be non-limiting, such that recitation of an item or items is not to the exclusion of other like items that can be substituted or added to the recited item(s).

What is claimed is:

1. A method of purifying one or more cannabinoids from a plant material of genus *cannabis*, comprising:
   adding the plant material of genus *cannabis* to ethanol;
   sonicating the ethanol and plant material of genus *cannabis* at a temperature of between about −80 to 30 degrees Celsius;
   dissolving cannabinoids in the ethanol to create a solution of cannabinoids;
   physically separating the plant material of genus *cannabis* from the solution comprising cannabinoids; and
   evaporating the ethanol from the solution at a pressure of less than 1 atmosphere.

2. The method of claim 1, comprising sonicating the ethanol and plant material of genus *cannabis* at a temperature of between about −50 to 10 degrees Celsius.

3. The method of claim 2, comprising sonicating the ethanol and plant material of genus *cannabis* at a temperature of between about −30 to −10 degrees Celsius.

4. The method of claim 1, comprising evaporating the ethanol from the solution at a temperature of between about 20 to 60 degrees Celsius.

5. The method of claim 1, comprising collecting a precipitated cannabinoid from within an ethanolic solution of cannabinoids.

6. The method of claim 5, comprising dissolving the precipitated cannabinoid in an alcohol, creating a second solution, then recrystallizing the precipitated cannabinoid from the second solution.

7. The method of claim 6, comprising evaporating alcohol from the second solution.

8. The method of claim 6, wherein the alcohol is ethanol.

* * * * *